United States Patent [19]

Behrstock

[11] Patent Number: 4,699,138

[45] Date of Patent: Oct. 13, 1987

[54] ENDOTRACHEAL INTUBATION SUCTION DEVICE

[76] Inventor: Barry Behrstock, 275 Victoria St., Costa Mesa, Calif. 92627

[21] Appl. No.: 890,350

[22] Filed: Jul. 25, 1986

[51] Int. Cl.$^4$ .......................................... A61M 16/00
[52] U.S. Cl. .............................. 128/207.16; 604/119; 604/902
[58] Field of Search ..................... 128/207.14, 207.15, 128/207.16; 604/118, 119, 902

[56] References Cited

U.S. PATENT DOCUMENTS

| 954,519 | 4/1910 | Kelly | 128/207.15 |
|---|---|---|---|
| 3,175,557 | 3/1965 | Hammond | 128/207.14 |
| 3,319,628 | 5/1967 | Halligan | 128/276 |
| 3,902,500 | 9/1975 | Dryden | 128/207.14 |
| 3,996,939 | 12/1976 | Sheridan et al. | 128/207.14 |
| 4,211,240 | 7/1980 | Gallagher | 604/119 |
| 4,488,548 | 12/1984 | Agdanowski | 128/207.15 |

FOREIGN PATENT DOCUMENTS 2350945 5/1974 Fed. Rep. of Germany ...... 604/119

OTHER PUBLICATIONS

"Modified Apparatur for Aspiration of Meconium from the Airway" by Louis E. Fazen, III, M.D., MPH, 1982, *Experience and Reason*, pp. 307–308.

"A Delivery Room Approach to the Meconium Aspiration Syndrome (MAS)" by William W. Fox, M.D., Brett B. Gutsche, M.D., Jay S. DeVore, M.D., *Clinical Pediatrics*, Apr. 1977, pp. 325–328.

"Suctioning of Upper Airway Meconium in Newborn Infants" by Jonathan E. Gage, M.D., H. William Taeusch, M.D., Salvador Treves, M.D., William Caldicott, M.D., JAMA, Dec. 4, 1981, pp. 2590–2592.

*Primary Examiner*—Henry J. Recla
*Attorney, Agent, or Firm*—Spensley Horn Jubas Lubitz

[57] ABSTRACT

An intubation suction device having first and second elongated tubular sections and a centrally located, uniquely configured handle is disclosed. The first section has an in-line port which has two functions. First, it acts as a suction valve to control suction. Second, its permits the easy introduction of a stylet through the device to an associated endotracheal tube. This latter feature enables the endotracheal tube to be easily inserted into the trachea region of a new born baby. By use of such device, expedited suction of material, such as meconium, from the oral, nasal, gastric and trachea regions of a newborn baby can be achieved.

8 Claims, 4 Drawing Figures

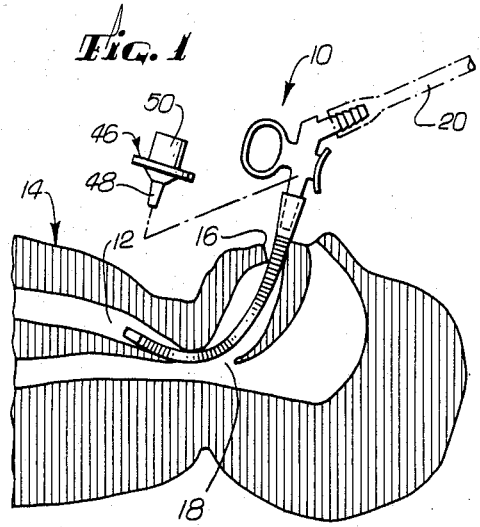
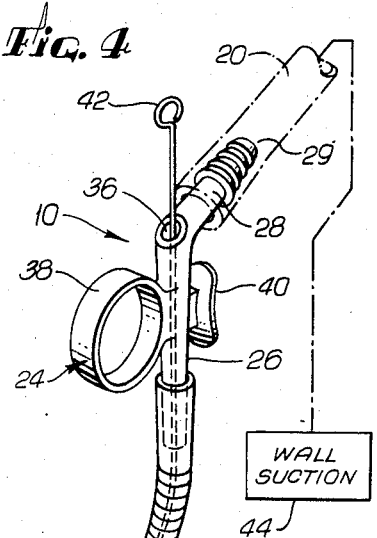
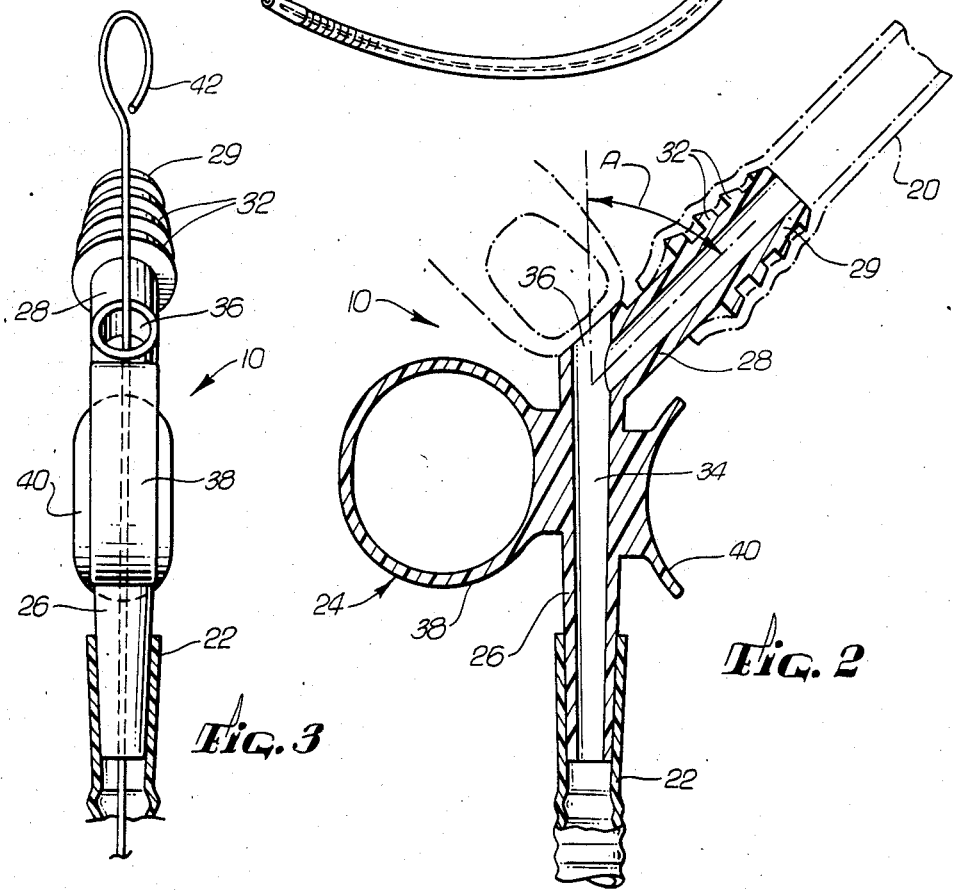

ENDOTRACHEAL INTUBATION SUCTION DEVICE

BACKGROUND OF THE INVENTION

1. Field of the Invention

This invention relates to the field of medical devices, and more specifically, to an endotracheal intubation device.

2. Prior Art

The need to remove meconium from a newborn infant is well recognized. Reference is made to articles published in the (i) *Journal of Pediatrics,* Dec. 1974, Vol. 85, No. 6, pp. 848-852 entitled "Meconium Aspiration in Infants—A Perspective Study", and (ii) *AM. J. Obstet. Gynecol.* 126:712, 1976, entitled "Combined Obstetric and Pediatric Approach to Prevent Meconium Aspiration Syndrome". In that latter article, Meconium Aspiration Syndrome (MAS) is indicated to be a variety of aspiration pneumonia which occurs most frequently in term or past-term newborn infants who have passed meconium in utero. The article indicates that such infants often develop progressive respiratory failure with significant hypoxemia during the first two-to-three days of life. Death rates as high as 28% have been reported for MAS. Indicated in the article is what is believed to be one of the most up-to-date methods for removing meconium from the newborn infant; to-wit: tracheal suction under direct laryngoscopic vision as soon as possible after the birth of the at-risk infant.

Intrapartum nasopharyngeal suction has also been added as an additional technique. Generally, as soon as the baby's head appears on the perineum, and prior to delivery of the shoulders, the doctor passes a suction catheter through the nares to the level of the nasopharynx and aspirates any mucous or meconium. The doctor then suctions the mouth and hypopharynx in a similar manner. Because the field into which the catheter is being passed (i.e., a baby's mouth and nose) is small, and irregular in shape, a flexible tubing is often used. Following the delivery, the doctor, with the aid of a laryngoscope, shines light and visualizes the area directly above and below the vocal cords looking for meconium. If it is present, it must be removed by a suction device (usually a standard endotracheal (E-T) tube often requiring an internal guide wire) as quickly as possible to try to avoid greater or deeper aspirations of this material.

Because proper placement of the E-T tube is critical, the infant is held in position and a doctor or other hospital personnel then inserts the E-T tube which may have a stiffening or guide wire inserted therein. The stiffening wire enables the otherwise flexible tube to be more readily inserted into the trachea. The stiffening wire is needed depending upon (i) the preference of the user, (ii) the positioning of the baby, and (iii) the difficulty of passing the E-T tube into the trachea which may be due to the angulation of the particular baby's oropharynx and trachea position or because the baby is struggling. Once in proper position, the stiffening wire must be removed in order to allow the doctor to suck out any meconium in the trachea region. The doctor places his mouth over the proximal end of the E-T tube while it is located in the trachea. Suction is achieved by, in effect, inhaling. Once this is done, the E-T tube is removed. If meconium is found in the tube, the doctor must reinsert the E-T tube in the trachea, again with the guide wire stylet, if desired, and repeat the suction process as often as needed until no further meconium is retrieved.

The problems with this approach are obvious. First, suction cannot be applied until the intubation process is complete and the guide wire, if used, is removed. This means that meconium and secretions above the cord cannot be suctioned without using a separate suction device. Further, the intubation process must sometimes be interrupted, time must be taken to suction the oropharynx (often just to see the tracheal opening) then the intubation process must be reinitiated. Secondly, since the mouth of the user is used to created the suction, this can lead to accidental ingestion. Third, the process must be repeated until all meconium is removed. The reintubation process requires the use of precious time until ventilation of the distressed infant can be initiated.

In response to these problems, the instant inventor developed a device which is set forth in U.S. Pat. No. 4,275,724, the disclosure of which is herein incorporated by reference. As set forth in the '724 patent, an endotracheal intubation device is disclosed which enables the user to simultaneously apply suction during the intubation process. By the use of that device, both the upper airways as well as the trachea region could be cleaned using a single apparatus.

While the '724 device does have a number of benefits, the present invention is directed to yet further improvements over the state-of-the-art. First, the device of the present invention permits the user to very accurately control the suction being applied, but without risk of ingesting meconium. The need for accurate control is well recognized. The need to prevent inhalation is a more recent problem. There is presently (the 1980', recognized to be an "AIDS" epidemic. The vertical transmission of this disease has been well documented from mother to unborn infant. Blood, as well as cervical and vaginal secretions, have all been shown to potentially carry this infectious virus. The references include *Hospital Practice,* Jun. 15, 1986, p. 127-155; "AIDS: What is Now Known II, Epidemiology."

Thus, the secretions of an infected newborn could potentially act as an infectious source of contamination and exposure to hospital personnel which come in contact with this material. Not only is the baby at risk because of the ingestion of meconium, but should a doctor ingest any of the meconium, then the doctor may face some risk of being exposed to AIDS virus, or some other communicable disease as well. Further, meconium is a nasty smelling and unpalatable material, and there may be some apprehension among doctors to apply direct suction. This is magnified enormously if there is a potential problem with contracting AIDS.

There also exists the risk of the user transmitting an infectious disease to the infant during the application of the user's mouth to the suction device. *Pediatric Infectious Disease,* Vol. 2, No. 2, Mar. 1984 Van Dyke, Russell, B., "Transmission of Herpes Simplex Virus, Type 1, To a New Born Infant During Endotracheal Suctioning For Miconium Aspirations."

The device of the present invention is also very straightforward in its design, and can be made at a relatively low cost. In addition, the device can be easily removed from the E-T tube after suction is completed, and if desired the E-T tube joined to a source of positive air pressure. Thus, the device can be used to achieve quick insertion of an E-T tube for purpose of meconium removal, or for supplying air during resuscitation.

One further advantage of the present device is that it permits suction of the oropharynx and mouth during the intubation process, but still permitting the user to gain those advantages associated with the use of a guide wire.

These and other advantages are achieved, while still permitting the device to be used and held in one hand, thereby freeing the other hand for holding a laryngoscope.

BRIEF SUMMARY OF THE INVENTION

An endotracheal intubation device is disclosed which enables the user to simultaneously apply suction during the intubation process. By the use of the device of the present invention, both the upper airways as well as the trachea region can be cleaned using a single apparatus. In addition, the device of the present invention allows for suction during direct visualization of the oropharynx and larynx. This enables the more accurate suction to the oropharynx and trachea regions and eliminates the need for repeated intubation or application of additional suction devices. In addition, the device of the present invention allows for these noted functions with a guide wire inserted at the user's discretion.

The present invention comprises a uniquely configured handle having first and second elongated tubular sections. The first tubular section has a first means for joining an endotracheal tube thereto. The second tubular section has a second means for joining a source of suction, such as wall suction, commonly found at a hospital. The uniquely configured handle defines a finger grip, a thumb rest and an orifice which can be selectively opened and closed, thereby regulating the suction in the E-T tube. The orifice also permits the easy introduction of a bendable wire stylet into the E-T tube. This enables the E-T tube to be held in position during insertion.

The novel features which are believed to be characteristic of this invention, both as to its organization and method of operation, together with further objectives and advantages thereof will be better understood from the following description considered in connection with accompanying drawings in which a presently preferred embodiment of the invention is illustrated by way of example. It is to be expressly understood, however, that the drawings are for the purpose of illustration and description only, and are not intended as a definition of the limits of the invention.

BRIEF DESCRIPTION OF THE DRAWINGS

FIG. 1 is a view showing the device of the present invention inserted into the trachea region of a baby;

FIG. 2 is a side cut-away plan view of the device;

FIG. 3 is a top plan view of the device;

FIG. 4 is a perspective view showing the device joined to a wall suction.

DETAILED DESCRIPTION OF THE INVENTION

Referring first to FIG. 1, one can see the device 10 of the present invention inserted into the trachea region 12 of a baby generally referred to by the numeral 14. As is shown in FIG. 1, the device 10 is passed through the mouth 16 through the oral airway 18, and into the trachea 12. While it may appear that this procedure could be easily performed, in practice it is most difficult. Generally, a highly trained nurse or physician would be responsible for inserting the device 10 into the oral airway 18 and trachea 12 so as to remove meconium or other undesirable materials from such regions. The physician would, as discussed in connection with the prior art, hold a laryngoscope in one hand while simultaneously attempting to properly insert the intubation device 10 with the other. As noted above, time is of the essence and should proper placement not be achieved during the first few attempts of inserting the device 10, it is believed that the probabilities associated with aspiration of meconium or other materials and subsequent hypoxia substantially increases.

Referring now to FIGS. 2, 3, and 4 the device 10 of the present invention is more fully illustrated. The device 10 is attached to suction tubing 20, which in turn is connected to a wall suction 44. Wall suction 44 is conventional and commonly found in hospitals. The basic element of the device 10 is the handle or grip means 24, and first and second tubular sections 26 and 28. Other elements which may also be considered as material to the device 10 are the endotracheal (E-T) tube 22 and the wire stylet 42. The E-T tube 22 is a commonly used, stock item in the art, and is made of a plastic having a predetermined curve which is configured so as to encourage insertion into the trachea 12. Such tubing is made of a variety of clear plastic materials as is also commonly known in the art.

Handle 24 is integrally formed on the first tubular section 26, which is in turn joined to the E-T tube 22. The second tubular section 28 is integrally joined to and in flow communication with the first tubular section 26. Section 28 is attached to the wall suction tubing 20. As can be seen, section 26 has a tapered nozzle or end 30 which permits section 26 to be easily, but securely slid into E-T tube 22. Nozzle end 29 of section 28 is also tapered and has a plurality outwardly extending ribs 32. Ribs 32 act to frictionally engage wall suction tubing 20 as illustrated in FIG. 2. Other means for joining the wall suction tubing 20 to the device 10 are also within the scope of the present invention.

Referring now to FIGS. 2, 3, and 4 one can see that the device 10 defines a curved or angled flow passageway 34 which extends through the first tubular section 26 and the second tubular section 28. An inline port 36 is formed in the first section 26, opposite end 30, in flow communication with passageway 34. In the preferred embodiment, port 36 is located at one end of section 26 adjacent the juncture of section 28. Port 36 enables suction to be selectively applied to the trachea region 12 of a baby as hereinbelow described in greater detail. Port 36 also enables stylet 42 to be readily inserted axially through section 26, and into E-T tube 22. The location of port 36 and the fact that stylet 42 can be easily inserted and removed from the E-T tube 22 represent advantages over the prior art.

As discussed above, one problem with many prior art devices was the inability to accurately control the suction as it was being applied to the trachea region 12. This problem is addressed by the configuration of handle 24 and the size and location of port 36. More specifically, handle 24 includes a ring 38 and arcuate thumb pad 40 which are arranged and configured on the first section 26 such that the device 10 can be easily and accurately held by a doctor while simultaneously controlling the vacuum being applied to the trachea region 12. As can be seen in FIG. 2, ring 38 is positioned on one side of section 26, while pad 40 is disposed on the opposite side. This arrangement permits the user to place his middle finger in the ring 38, the thumb on pad 40, and the index finger over port 36, as desired.

Port 36 is located and sized such that it can easily be covered or uncovered by the user's index finger in the preferred embodiment. The diameter of port 36 is selected such that when uncovered, there is substantially no suction created at the end 22a of E-T tube 22.

In the preferred embodiment of the present invention, section 28 is angled (A) with respect to section 26 by appoximately 30°-60°, with 45° being the preferred angle. This angle has been found to enable the user to easily open and close port 36 by using one's index finger as a stop element. Further, the positioning of finger ring 38, just posterior to pad 40 allows for comfortable placement of the index finger over port 36, when held in the usual manner during intubation. As also can be seen in FIGS. 2 and 3, wire stylet 42 extends through port 36, along the length of section 26 and through the E-T tube 22. Stylet 42 can be bent into various shapes so as to give further rigidity to the configuration of the E-T tube 22. In this manner, the E-T tube 22 will conform to a specific configuration, thus making it easier for the user to insert tube 22 into the desired region of the trachea 12.

The operation of the device 10 of the present invention will now be described.

In the preferred embodiment, section 28 is connected to a suction device 44 by means of conduit 20. The E-T tube 22 is joined to section 26. If desired, the stylet 42 is axially inserted through port 36, along part of flowpath 34 and into the E-T tube 22. Both the stylet 42 and the E-T tube are then shaped into a desired configuration. With the aid of a laryngoscope, insertion of the device 10 begins. However, because only one hand is needed to hold the device 10, the doctor can more accurately direct the laryngoscope and simultaneously apply suction during the entire intubation process. For example, as the E-T tube 22 is inserted and should the doctor see any meconium in the mouth region, it could be sucked out. This would be achieved by merely placing the index finger over port 36, and the suction would be channeled along the length of the E-T tube 22 to end 22a. The ring 38 and pad 40 enable the user to quickly direct the E-T tube 22 to a desired location. Further, the entire device 10 is compact enough such that it does not interfere with direct visualization of a baby's mouth and trachea region. As the device 10 proceeds down the oral airway 18 into the trachea region 12, any meconium can likewise be removed. In the preferred embodiment port 36 is large enough such that even with stylet 42 in place, substantially no suction is created in the E-T tube 22. However, if port 36 is closed off, a suction would be created. Thus, during insertion and without removal of the stylet 42, closing off port 36 enables suction to be created in E-T tube 22. This is a significant advance of the art as meconium can be removed during the intubation procedure, and without the device 10 being removed. Once in place in the trachea region 12, the stylet 42 is preferably removed, so as to create substantially unobstructed flow from region 12, through the device 10, along path 34. At any time the doctor needs to discontinue suction, he/she needs merely to remove the blockage of port 36 and virtually all of the suction being created in the E-T tube 22 would be directed out port 36.

In alternate embodiments, rather than using a wall suction, the device of the present invention can be joined to a suction trap such as a "De-Lee" trap well known in the art.

Yet another advantage of the present invention is that if no meconium is found in the mouth or trachea region, once the device 10 is in place, in many instances it is necessary to intubate the child. That is, to force air into the child's lungs. Since the E-T tube 22 is already in the trachea region 12, handle 24 can easily be removed from E-T tube 22, and generally tubular adapter 46 put in its place. As illustrated in FIG. 1, adapter 46 has a nozzle 48 at one end which is inserted into the E-T tube 22 means 50 for joining the adaptor 46 to a conventional air bag (not shown) which is located at the other end. Adapter 46 when formed to E-T tube 22 can be used to force air with or without additional oxygen into the baby's lungs. In this manner, there is no need to remove the already-in-place E-T tube 22 so as to supply air to the baby. Thus, the time until a baby is properly ventilated is kept to a minimum. It is anticipated that the device 10, E-T tube 22 and adaptor 46 will be packaged and potentially used together. Such combination will enable the user to respond to both removal of undesirable materials from a baby's trachea region and to supply air/oxygen during ventilation.

While this invention has been described with reference to specific embodiments, it should be understood that other embodiments are also within the scope of the present invention. This invention, therefore, is not intended to be limited to the particular embodiments herein disclosed.

I claim:
1. An intubation suction device, comprising:
   (a) first and second tubular sections defining a flow passage through said device, said first tubular section having a first means for joining an endotracheal tube thereto, said second tubular section, acutely angled with respect to said first tubular section, having a second means for joining said device to a source of suction;
   (b) a centrally located handle means, disposed on said first tubular section, including a finger grip and an opposed thumb rest; and wherein,
   (c) said device defines a port located axially in line on said first tubular section and in flow communication with said flow passage such that closing said port permits suction to be created in said first tubular section, and opening said port releases the suction formed in said first tubular section.

2. The device of claim 1 further including a curved endotracheal tube and wherein said first tubular section is joined to said curved endotracheal tube.

3. The device of claim 1 further including a suction conduit and wherein said second tubular section is joined to said suction conduit.

4. The device of claim 1 further including an elongated stylet disposed through said port and extending into said first tubular section.

5. The device of claim 1 wherein said second tubular section is acutely angled with respect to said first tubular section from approximately 30° to about 60°.

6. An intubation suction device, comprising an elongated, acutely shaped conduit having first and second ends, said conduit defining a flow passageway, a curved endotracheal tube joined to said first end, a suction tube joined to said second end, a centrally located handle disposed on said shaped conduit, said handle having a ring-shaped finger grip and an opposed arcuate thumb rest, and wherein said device defines a port in flow communication with said passageway for controlling suction in said endotracheal tube, said port being configured such that a substantially straight in-line flow path is defined between said port and said first end of said conduit.

7. The device according to claim 6 further including an elongated stiffening means disposed through said port and extending into said endotracheal tube.

8. An intubation/ventillation system comprising:
  (a) an intubation suction device having:
    (i) first and second tubular sections defining a flow passage through said device, said first tubular section having a first means for joining an endotracheal tube thereto, said second tubular section, acutely angled with respect to said first tubular section, having a second means for joining said device to a source of suction;
    (ii) a centrally located handle means, disposed on said first tubular section, including a finger grip and an opposed thumb rest; and wherein,
    (iii) said device defines a port located axially in line on said first tubular section and in flow communication with said flow passage such that closing said port permits suction to be created in said first tubular section, and opening said port releaves the suction formed in said first tubular section;
  (b) a curved endotracheal tube selectively joined to said intubation device; and
  (c) a flow adapter having a shaped nozzle selectively joined to said endotracheal tube, after removal of said endotracheal tube from said suction device and means for joining said adapter to a source of positive pressure.

* * * * *